United States Patent [19]

Zimmerman

[11] 4,284,635

[45] * Aug. 18, 1981

[54] ANALGESIC 1,2,4,5-TETRA-ALKYL-4-ARYLPIPERIDINES

[75] Inventor: Dennis M. Zimmerman, Mooresville, Ind.

[73] Assignee: Eli Lilly and Company, Indianapolis, Ind.

[*] Notice: The portion of the term of this patent subsequent to Mar. 28, 1995, has been disclaimed.

[21] Appl. No.: 965,137

[22] Filed: Nov. 29, 1978

[51] Int. Cl.³ ................. A61K 31/445; C07D 211/22; C07D 211/14

[52] U.S. Cl. .................................... 424/267; 546/192; 546/236; 546/240; 546/339; 546/344; 546/348; 546/350

[58] Field of Search ...................... 546/240, 192, 236; 424/267

[56] References Cited

U.S. PATENT DOCUMENTS

| | | | |
|---|---|---|---|
| 2,892,842 | 6/1959 | McElvain | 546/240 |
| 2,956,058 | 10/1960 | Shepard et al. | 546/236 |
| 3,043,845 | 7/1962 | Zaugg et al. | 546/225 |
| 3,080,372 | 3/1953 | Janssen | 546/225 |
| 3,324,139 | 6/1967 | Kugita et al. | 546/240 |
| 3,325,502 | 6/1967 | Kugita et al. | 546/240 |
| 3,574,219 | 4/1971 | Kugita et al. | 546/240 |
| 3,936,468 | 2/1976 | Yamamoto et al. | 424/267 X |
| 4,081,450 | 3/1978 | Zimmerman | 546/240 X |

FOREIGN PATENT DOCUMENTS

| | | | |
|---|---|---|---|
| 833044 | 3/1976 | Belgium | 546/192 |
| 41-20947 | 12/1966 | Japan | 546/240 |

OTHER PUBLICATIONS

McElvain, S. et al., J. Am. Chem. Soc., 80, 3915 (1958).
Kugita, H., et al., J. Med. Chem., 8, 313 (1965).
Jacoby, R., et al., J. Med. Chem., 17, 453 (1974).
Kugita, H., et al., J. Med. Chem., 7, 298 (1964).

Primary Examiner—Henry R. Jiles
Assistant Examiner—Richard A. Schwartz
Attorney, Agent, or Firm—Karen O'Connor; Charles W. Ashbrook; Arthur R. Whale

[57] ABSTRACT

4-Phenylpiperidines bearing substituents at the 1,2,4 and 5-positions are potent analgesics. Pharmaceutical formulations containing such compounds and a method for effecting analgesia are provided.

22 Claims, No Drawings

ANALGESIC 1,2,4,5-TETRA-ALKYL-4-ARYLPIPERIDINES

BACKGROUND OF THE INVENTION

4-Arylpiperidines have long been recognized as a valuable class of compounds capable of effecting the central nervous system in animals. Several 4-phenylpiperidines having various substituents attached to the piperidine ring are known. McElvain et al., for example, disclose a number of 1-methyl-4-alkyl-4-arylpiperidines in U.S. Pat. No. 2,892,842. In *J. Am. Chem. Soc.*, 80, 3915-3923 (1958), McElvain et al. reported the preparation of 1,3,4-trimethyl-4-(2-methoxyphenyl)piperidine as a bi-product in the synthesis of a 1,4-dialkyl-4-arylpiperidine. A number of 1,2,3-trialkyl-3-arylpiperidines have been reported as analgesic drugs, see U.S. Pat. Nos. 3,043,845 and 2,892,842. Similarly, various 1-aroyl-3,4-dialkyl-4-arylpiperidines have been reported to be useful as central nervous system depressants, U.S. Pat. No. 3,080,372. It recently has been discovered that not only is an alkyl group located in the piperidine 3-position important for unique biological activity, but also that separation of optical isomers provides compounds displaying narcotic agonist activity and mixed agonist-antagonist activity, see U.S. Pat. No. 4,081,450.

An object of this invention is to provide 4-arylpiperidines which are more highly substituted in the piperidine ring than any of the prior art compounds.

SUMMARY OF THE INVENTION

This invention provides 1,2,4,5-tetra-alkyl-4-arylpiperidines which are useful as analgesics. The invention is more particularly directed to 4-phenylpiperidines having the formula:

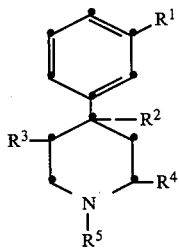

wherein:
$R^1$ is hydrogen, hydroxy or methoxy;
$R^2$, $R^3$ and $R^4$ independently are $C_1$–$C_5$ alkyl;
$R^5$ is $C_1$–$C_{10}$ alkyl, benzyl or $CH_2R^6$, in which $R^6$ is $C_2$–$C_7$ alkenyl or $C_3$–$C_6$ cycloalkyl; and the pharmaceutically acceptable acid addition salts thereof.

Also contemplated by this invention are pharmaceutical formulations containing the analgesically active compounds defined by the above formulas combined with a suitable pharmaceutical carrier. Said formulations are useful in the treatment of pain and related CNS disorders.

Also included within the scope of this invention is a method of treating pain comprising administering to an animal an analgesically effective amount of a 4-phenylpiperidine having the above formula.

A further embodiment of the invention are intermediates useful in preparing the analgesics defined by the above formula. Specifically provided are piperidines of the formula

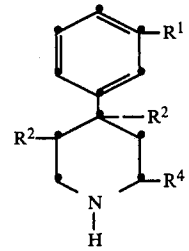

wherein $R^1$, $R^2$, $R^3$ and $R^4$ have the above-defined meanings. Additionally provided are tetrahydropyridinium salt intermediates of the formula

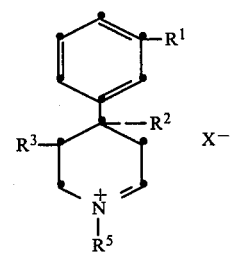

wherein $R^1$, $R^2$, $R^3$ and $R^5$ are as defined above, and $X^-$ is a suitable anion.

DETAILED DESCRIPTION OF THE INVENTION

As used herein, $R^2$, $R^3$ and $R^4$ independently are $C_1$–$C_5$ alkyl such as methyl, ethyl, n-propyl, isopropyl, n-butyl, isobutyl, sec-butyl, n-pentyl, isopentyl and the like. Preferred piperidines are those wherein $R^2$, $R^3$ and $R^4$ are selected from normal alkyl groups, such as n-propyl for example. A particularly preferred group of piperidines according to this invention are those wherein $R^3$ is methyl or ethyl, and $R^2$ and $R^4$ independently are n-alkyl such as methyl, ethyl or n-propyl.

In the formula defining the compounds of this invention, $R^5$ includes $C_1$–$C_{10}$ alkyl groups such as methyl, ethyl, n-propyl, isopropyl, n-pentyl, isohexyl, 2,3-dimethylheptyl, 2-ethylhexyl, n-octyl, n-decyl, and 2,3-diethylhexyl. A preferred group of alkyl substituents falling within the term "$C_1$–$C_{10}$ alkyl" includes $C_1$–$C_5$ alkyl groups such as methyl, ethyl, n-propyl, isobutyl and n-pentyl.

$R^5$ additionally includes alkenyl and cycloalkylmethyl groups defined by the part-structure $CH_2R^6$ in which $R^6$ is $C_2$–$C_7$ alkenyl or $C_3$–$C_6$ cycloalkyl. Typical alkenyl groups contemplated include allyl, 3-butenyl, 2-methyl-2-butenyl, 3-pentenyl, 3-heptenyl, 5-hexenyl and the like. Routinely used cycloalkylmethyl groups include cyclopropylmethyl, cyclobutylmethyl, cyclopentylmethyl and cyclohexylmethyl.

Included within the group of compounds contemplated by this invention are the pharmaceutically acceptable acid addition salts of the tetra-alkyl piperidine bases defined by the above formula. Such salts are those made with commonly used inorganic acids such as hydrochloric, hydrobromic, sulfuric, perchloric, phosphoric, and related acids. Organic acids can similarly be used to form the salts of this invention, and commonly used organic acids include acetic, maleic, picric, benzoic, succinic, citric, ascorbic and related acids. The piperidines of the invention additionally form quaternary ammonium salts with a number of alkylating agents such as methyl chloride, ethyl bromide, allyl iodide, dimethyl sulfate, and the like.

The tetra-alkyl piperidines provided by this invention are derived from 1,3,4-trisubstituted piperidines by reaction first with a dehydrogenating oxidizing agent to afford a 1,3,5-trisubstituted-1,4,5,6-tetrahydropyridine; then double bond migration by salt formation to form a reactive intermediate which is receptive to an alkali metal alkylating agent; and finally alkylation with such alkali metal alkylating agent. The process thus outlined can be depicted by the following scheme:

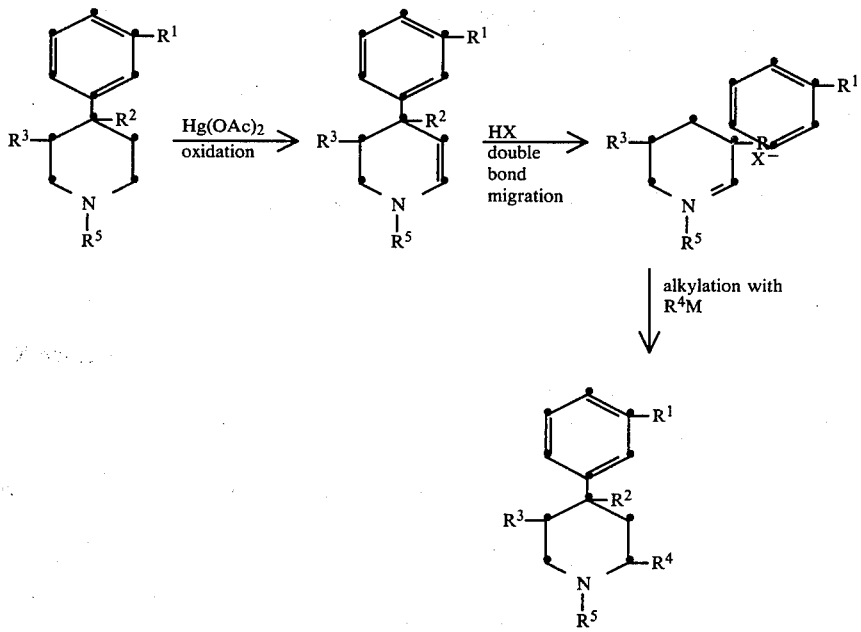

In the above formulas, $R^1$, $R^2$, $R^3$, $R^4$ and $R^5$ have the above-defined meanings. X is an anion and M is a cation such as an alkali metal cation.

The required starting materials for preparing the tetra substituted piperidines of this invention are 1,3,4-trisubstituted-4-arylpiperidines. Such compounds are available by the process of U.S. Pat. No. 4,081,450. The trisubstituted piperidines are reacted with an oxidizing agent capable of dehydrogenating the piperidine to provide a 1,4,5-trisubstituted-4-aryl-1,4,5,6-tetrahydropyridine. Since the piperidine starting material is a cyclic tertiary amine, it can be readily oxidized to the corresponding enamine by reaction with a four molar amount of mercuric acetate in five percent aqueous acetic acid according to the general method of Leonard et al., J. Am. Chem. Soc., 77, 439 (1955); 78; 3457 (1956) and 78, 3463 (1956). When the reaction is carried out at about 50° to about 150° C., it normally is substantially complete within about 6 to about 10 hours. The product, an enamine, namely a trisubstituted-4-aryl-1,4,5,6-tetrahydropyridine, is generally recovered by decomposing any remaining oxidizing agent and biproducts, in the case of mercuric acetate by adding excess hydrogen sulfide to the reaction mixture, and then filtering the mixture to remove the precipitated mercurous acetate and mercuric sulfide complex. The filtrate is then made alkaline, for instance by the addition of a base such as sodium hydroxide or potassium carbonate, and the product is extracted therefrom into a suitable water immiscible solvent such as diethyl ether, dichloromethane, ethyl acetate or the like. The tetrahydropyridine so formed can be further purified if desired by routine methods such as chromatography or distillation. Typical 1,4,5,6-tetrahydropyridines prepared by such oxidation process include:

1,4-dimethyl-5-ethyl-4-phenyl-1,4,5,6-tetrahydropyridine;

1,4-di-n-propyl-5-methyl-4-(3-methoxyphenyl)-1,4,5,6-tetrahydropyridine;

1-benzyl-4,5-dimethyl-4-phenyl-1,4,5,6-tetrahydropyridine;

1,-allyl-4-n-butyl-5-n-propyl-4-(3-hydroxyphenyl)-1,4,5,6-tetrahydropyridine;

1-cyclopropylmethyl-4-ethyl-5-methyl-4-(3-methoxyphenyl)-1,4,5,6-tetrahydropyridine; and related enamines.

Reaction of the trisubstituted-4-aryl-1,4,5,6-tetrahydropyridine thus formed with an acid effects salt formation with concomittant double bond migration to afford an iminium salt, namely a 1,4,5-trisubstituted-4-aryl-3,4,5,6-tetrahydropyridinium salt. Any of a number of inorganic and organic acids can be utilized to effect the salt formation and double bond migration, and commonly used acids include hydrobromic acid, hydrochloric acid, perchloric acid, sulfuric acid, tetrafluoroboric acid, phosphoric acid, para-toluenesulfonic acid, and the like.

The formation of the iminium salt generally is effected by simply dissolving the appropriate 1,4,5,-trisubstituted-4-aryl-1,4,5,6-tetrahydropyridine in an excess of a suitable acid and permitting the reaction mixture to stand for several minutes at a temperature of about 0° to about 30° C. The iminium salt normally crystallizes from the acid solution and can be collected by filtration. As an illustration, a tetrahydropyridine such as 1-cyclopropylmethyl-4-ethyl-5-n-propyl-4-(3-methoxyphenyl)-1,4,5,6-tetrahydropyridine can be dissolved in an acid such as tetrafluoroboric acid, utilizing a suitable co-solvent such as diethyl ether or ethyl acetate if desired. The iminium salt forms almost immediately and crystallizes out of solution within about one hour. Filtration of the reaction mixture provides the corresponding iminium salt, for example 1-cyclopropylmethyl-4-ethyl-5-n-propyl-4-(3-methoxyphenyl)-3,4,5,6-tetrahydropyridinium tetrafluoroborate. The salt thus formed can be further purified if desired by recrystallization from solvents such as ethyl acetate, ethanol, acetone and the like.

The iminium salts thus formed are important intermediates in the preparation of the biologically active compounds of the invention. Such iminium salts are defined by the formula

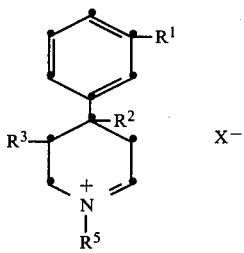

wherein:
$R^1$ is hydrogen, hydroxy or methoxy;
$R^2$ and $R^3$ independently are $C_1$-$C_5$ alkyl;
$R^5$ is $C_1$-$C_{10}$ alkyl, benzyl or $CH_2R^6$ wherein $R^6$ is $C_2$-$C_7$ alkenyl or $C_3$-$C_6$ cycloalkyl; and
$X^-$ is a suitable anion such as chloride, bromide, iodide, perchlorate, tetrafluoroborate, phosphate, sulfate, para-toluenesulfonate, acetate, nitrate, and the like.

The iminium salt intermediate next is alkylated by reaction with a $C_1$-$C_5$ alkylide reagent. An "alkylide reagent" as used herein means any reagent capable of providing a source of nucleophilic $C_1$-$C_5$ alkyl carbanion groups. Typical of such reagents are the alkali metal $C_1$-$C_5$ alkyl metalides such as butyl lithium, ethyl sodium, methyl lithium, n-propyl potassium, isobutyl lithium, isopentyl sodium and the like. Additional alkylides include $C_1$-$C_5$ Grignard reagents such as methyl magnesium bromide and n-butyl magnesium bromide, as well as di-$C_1$-$C_5$ alkyl lithium cuprates such as diethyl lithium cuprate and the like.

The alkylation reaction to provide the tetrasubstituted piperidines of this invention is carried out by mixing a suitable $C_1$-$C_5$ alkylide reagent with a 1,4,5-trisubstituted-4-aryl-3,4,5,6-tetrahydropyridinium salt. The alkylide reagent typically is utilized in greater than one molar excess, for instance from one to about one hundred molar excess relative to the iminium salt. The alkylation can be conducted in any of a number of organic solvents, including diethyl ether, tetrahydrofuran, benzene, dichloromethane, dioxane and the like. The reaction normally is substantially complete within about one to ten hours when carried out at a temperature of about 20° to 40° C. The product, a tetrasubstituted-4-arylpiperidine of the invention, can be readily isolated by decomposing any unreacted alkylating agent, for instance by washing the reaction mixture with aqueous ammonium chloride or the like. The organic layer then is separated and the solvent is evaporated therefrom to provide the 1,2,4,5-tetrasubstituted-4-aryl-piperidine of the invention. Such compound can be further purified if needed by routine methods such as chromatography, distillation, crystallization and the like.

As noted before, the piperidines provided by this invention are basic compounds and as such form salts with any of a number of acids. The pharmaceutically acceptable salts formed with inorganic acids and organic acids comprise an additional embodiment of this invention. The salts thus contemplated are those which are substantially as non-toxic as the free bases from which they are derived. The salts thus provided are prepared by reacting the tetra-substituted-4-aryl-piperidine with about an equimolar quantity or excess of an acid such as hydrochloric acid, hydrobromic acid, maleic acid, acetic acid, citric acid, or the like. The salts so prepared are highly crystalline and thus lend themselves to ready purification by recrystallization from solvents such as ethanol, water, ethyl acetate and the like. Treatment of a piperidinium salt with a base such as sodium hydroxide or potassium carbonate readily affords the free base.

Also contemplated are the quaternary piperidinium salts prepared by reacting the free piperidine base with an alkylating agent such as methyl chloride, dimethyl sulfate, ethyl bromide, and the like. Such salts also are highly crystalline and are easily purified by recrystallization from common solvents.

Not all of the biologically active piperidines provided by the invention need to be prepared directly from 1,3,4-trisubstituted-4-aryl-piperidines. An alternative method of preparation involves simple alkylation of a 2,4,5-trialkyl-4-arylpiperidine. The later compound is derived from a 1,2,4,5-tetrasubstituted-4-arylpiperidine of the invention wherein the 1-substituent is removable to provide an intermediate of the formula

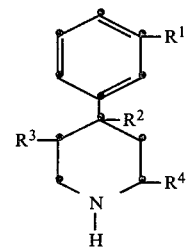

in which $R^1$, $R^2$, $R^3$ and $R^4$ are as defined hereinabove. Typical 1-substituents which are readily removable include methyl and benzyl. For example, 1-benzyl-4,5-dimethyl-4-phenylpiperidine can be dehydrogenated by reaction with mercuric acetate to provide 1-benzyl-4,5-dimethyl-4-phenyl-1,4,5,6-tetrahydropyridine. Double bond migration and salt formation can be carried out to give, for example, 1-benzyl-4,5-dimethyl-4-phenyl-3,4,5,6-tetrahydropyridinium tetrafluoroborate. Alkylation of the iminium salt thus formed, for instance by reaction with n-propyl lithium, provides 1-benzyl-2-n-propyl-4,5-dimethyl-4-phenylpiperidine. The 1-benzyl group of such compound is readily removed by hydrogenation in the presence of a catalyst such as platinum or palladium on carbon, thus affording a 1-unsubstituted piperidine intermediate, namely 2-n-propyl-4,5-dimethyl-4-phenylpiperidine. Such intermediate can then be alkylated with any $R^5$ alkylating agent, wherein $R^5$ is as defined above. Typical alkylating agents include $R^5$-halides such as methyl bromide, allyl iodide, cyclopropylmethyl chloride, n-decyl iodide, 3-pentenyl iodide, isoheptyl bromide and the like.

The alkylation of a 2,4,5-trisubstituted-4-arylpiperidine is accomplished by commingling approximately equimolar quantities of the piperidine and alkylating agent in a suitable unreactive solvent such as acetone, diethyl ether, dimethyl sulfoxide, ethanol or the like. A base such as sodium bicarbonate or triethylamine normally is utilized in the alkylation reaction to act as an acid scavenger. The reaction typically is carried out at a temperature of about 20° to about 100° C., and usually is complete within about 1 to about 4 hours. The alkylated product, a 1,2,4,5-tetrasubstituted-4-arylpiperidine of the invention, can be readily isolated by simply removing the reaction solvent and crystallizing the product from a solvent such as diethyl ether. If desired the piperidine can be converted to an acid addition salt in the conventional manner.

The tetrasubstituted-4-(3-hydroxyphenyl)piperidines of this invention (compounds of the above formula wherein $R^1$ is hydroxy) can be prepared directly from 1,4,5-trisubstituted-4-(3-hydroxyphenyl)piperidines. Such compounds preferably are prepared, however, directly from the corresponding 1,2,4,5-tetrasubstituted-4-(3-methoxyphenyl)piperidines of the invention. In other words, it is convenient to first prepare large quantities of 2,4,5-trisubstituted-4-(3-methoxyphenyl)piperidines, and then use such compounds for alkylation with various $R^5$ groups as hereinbefore described, and then to de-methylate the 4-(3-methoxyphenyl) group so as to provide a variety of 1,2,4,5-tetrasubstituted-4-(3-hydroxyphenyl)piperidines. Such de-methylation can be accomplished by simply reacting the methoxyphenyl substituted piperidines with hydrobromic acid and acetic acid. Such de-methylation reactions are well known in the art, see particularly U.S. Pat. Nos. 3,324,139 and 4,081,450. As an illustration, a piperidine such as 1-n-hexyl-2-ethyl-4-n-propyl-5-n-butyl-4-(3-methoxyphenyl)piperidine can be dissolved in excess forty-eight percent aqueous hydrobromic acid and acetic acid and the reaction mixture can be heated to about 100° C. for about twelve hours to effect total cleavage of the methyl ether moiety. The product, for instance 1-n-hexyl-2-ethyl-4-n-propyl-5-n-butyl-4-(3-hydroxyphenyl)piperidine, is isolated by simply neutralizing the acidic reaction mixture and extracting the product into a solvent such as ethyl acetate or diethyl ether. Evaporation of the organic solvent then provides the desired compound, generally as a crystalline solid.

It should be noted that the tetrasubstituted piperidines provided by this invention can exist in several isomeric forms. For example, the $R^4$ alkyl group can be positioned above the plane of the piperidine ring while the $R^2$ and $R^3$ alkyl groups both are oriented below the plane of the ring. Alternatively, the $R^3$ and $R^4$ alkyl groups can be oriented cis to one another and positioned, for example, above the plane of the piperidine ring, while the $R^2$ group is oriented below the plane. All separate isomers, and racemic mixtures thereof, are contemplated by this invention.

As previously pointed out, the starting materials for preparing the compounds of this invention are 1,3,4-trisubstituted-4-arylpiperidines, which in turn are made by the process of U.S. Pat. No. 4,081,450. Such starting compounds are available in both cis and trans forms, the cis isomer being the compound wherein both alkyl groups at the 3 and 4 positions of the piperidine ring are positioned on the same side of the plane of the ring. The trans isomer of course has the 3- alkyl substituent on the side of the ring opposite to that of the 4-alkyl substituent. By starting with a pure cis or pure trans 1,3,4-trialkyl-4-arylpiperidine, there is prepared according to this invention a racemic mixture of two 1,2,4,5,-tetra-substituted-4-arylpiperidines. If desired, the racemates can be separated by conventional means such as fractional crystallization and chromatography.

Typical 1,2,4,5-tetra-substituted-4-arylpiperidines provided by this invention include the following:

1-ethyl-2-methyl-4-isopropyl-5-n-propyl-4-phenyl-piperidine;
1-(2,3-dimethylheptyl)-2,4-dimethyl-5-n-propyl-4-(3-hydroxyphenyl)piperidine;
1-cyclopropylmethyl-2,4,5-triethyl-4-(3-methoxyphenyl)piperidine;
1-allyl-2,4,-di-n-propyl-5-methyl-4-(3-hydroxyphenyl)-piperidine;
1-(5-hexenyl)-2-methyl-4,5-diethyl-4-(3-methoxyphenyl)piperidine;
1-n-decyl-2,4,5-tri-n-butyl-4-phenylpiperidine;
1-cyclohexylmethyl-2-ethyl-4,5-di-n-pentyl-4-(3-hydroxyphenyl)piperidine;
1-cyclopentylmethyl-2-n-pentyl-4,5-dimethyl-4-(3-methoxyphenyl)piperidine;
1,2-dimethyl-4,5-di-n-propyl-4-phenylpiperidine;
1-benzyl-2-methyl-4,5-diethyl-4-(3-hydroxyphenyl)-piperidine;
1-iso-octyl-2,4-dimethyl-5-n-butyl-4-phenyl-piperidinium bromide;
1-n-pentyl-2,4,5-trimethyl-4-(3-methoxyphenyl)-piperidinium chloride;
1,2,4,5-tetramethyl-4-phenylpiperidinium para-toluenesulfonate;
1-ethyl-2,4-di-n-propyl-5-methyl-4-(3-hydroxyphenyl)-piperidinium oxalate;
1,2-dimethyl-4,5-diethyl-4-phenylpiperidinium methanesulfate;
1,1,2-trimethyl-4,5-diethyl-4-phenylpiperidinium bromide;
1-(2-methyl-4-hexenyl)-1-methyl-2,4,5-triethyl-4-phenylpiperidinium chloride;
1-benzyl-2,4,5-tri-n-propyl-4-phenylpiperidine; and
1-(3-octenyl)-2,4,5-trimethyl-4-phenylpiperidine.

The 1,2,4,5-tetra-substituted-4-arylpiperidines provided by this invention are valuable analgesics capable of treating animals suffering from pain. The compounds are comparable to meperidine in analgesic potency, as demonstrated for instance in the standard mouse writhing assay. The compounds are not "morphine-like", however, when tested in mice, and have demonstrated narcotic antagonist-like properties.

The analgesic activity of a number of compounds provided by this invention has been determined in the standard rat-tail jerk assay and the mouse writhing assay. Table I which follows presents typical test results obtained with the claimed compounds. The results in the mouse writhing assay are presented as the effective dose in mg./kg. of the tested compound required to inhibit induced writhing in the test animals by fifty percent ($ED_{50}$). Results are presented in Column II for both subcutaneous (S.C.) and oral (p.o.) administration of the test compound recited in Column I.

Column III presents the effects of the claimed compounds on rats subjected to a heat sensation. The compounds recited in column I were administered subcutaneously to the test animals. The test results are reported as the minimum effective dose (MED) of compound in mg./kg. needed to delay response to the pain stimulus by one second compared to control animals.

TABLE I

| Column I | Column II Mouse Writhing ED$_{50}$ | | Column III Rat Tail Jerk |
|---|---|---|---|
| | s.c. | p.o. | MED$_1$ sec. |
| Meperidine | 2.8 | 21 | 3.0 |
| 1,2,4,5-tetramethyl-4-(3-methoxyphenyl)piperidine | 19.0 | 16.0 | 10 |
| 1,2,4,5-tetramethyl-4-(3-hydroxyphenyl)piperidine | 1.25 | 9.2 | 1 |
| 1,2,5-trimethyl-4-(n-propyl)-4-(3-methoxyphenyl)piperidine | 4 | 11.5 | 2 |
| 1,2,5-trimethyl-4-(n-propyl)-4-(3-hydroxyphenyl)piperidine | 29.0 | 16.0 | 20 |

A further aspect of this invention includes pharmaceutical formulations containing the 1,2,4,5-tetrasubstituted-4-arylpiperidine analgesics having the above formula. Such formulations are useful in the treatment of pain in animals, including human subjects. The formulations contemplated comprise an analgesically effective dose of a piperidine of the invention in combination with any of a number of pharmaceutical diluents, excipients and carriers. Typical diluents commonly used in such formulations include lactose, sucrose, starch, micro-crystalline cellulose, calcium sulfate, sodium benzoate and the like. Typical formulations will contain from about 1 to about 30 percent by weight of active ingredient. The formulations can be compressed into tablets or encapsulated in gelatin capsules for convenient oral administration. Alternatively, the formulations can be dissolved in sterile water or saline and placed in a suitable vial for convenient intravenous or intramuscular administration.

The tetrasubstituted-4-aryl piperidines of the invention have demonstrated valuable analgesic activity, and therefore are useful in the treatment of pain. The invention thus further provides a method for imparting analgesia in an animal which comprises administering an analgesically effective dose of a compound of the invention. Typical doses commonly administered will range from about 0.5 to about 150 mg. per kg. of animal body weight. A preferred dose will be from about 1.0 to about 50 mg./kg. The method of treatment can be accomplished by administering an analgesic compound of the invention via the oral or parenteral routes. Preferred routes of administration include the oral and intramuscular routes. Subcutaneous administration of the suitably formulated active compounds can also be utilized when desired. As an illustration of the contemplated method of treatment, a formulation comprising about 50 mg. of 1,2,5-trimethyl-4-n-propyl-4-(3-hydroxyphenyl)-piperidinium chloride dissolved in about 1 ml. of saline is administered from 1 to 4 times daily to a subject suffering from pain and in need of analgesic treatment.

In an effort to more fully illustrate the operation of this invention, the following detailed examples are provided. The examples are illustrative only and are not intended to limit the scope of the invention.

EXAMPLE 1

Preparation of 1,4,5-trimethyl-4-(3-methoxyphenyl)-1,4,5,6-tetrahydropyridine

A solution of 5.2 g. of 1,4,5-trimethyl-4-(3-methoxyphenyl)piperidine in 100 ml. of five percent aqueous acetic acid containing 34.2 g. of mercuric acetate was heated to 85° C. and stirred for eight hours. The reaction mixture next was cooled to room temperature and filtered. The filtrate was stirred and saturated with excess hydrogen sulfide for twenty-five minutes, and then stirring was continued for an additional thirty minutes. After filtering the reaction mixture twice through super flow filter aid, the filtrate was made alkaline with fifty percent sodium hydroxide. The alkaline solution was extracted several times with diethyl ether, and the ethereal extracts were combined, washed with water and dried. Removal of the solvent by evaporation under reduced pressure afforded 4.11 g. of the product as an oil. The oil was distilled to provide 2.0 g. of 1,4,5-trimethyl-4-(3-methoxyphenyl)-1,4,5,6-tetrahydropyridine. B.P. 114°–118° C. at 0.1 torr.

EXAMPLE 2

1,4,5-Trimethyl-4(3-methoxyphenyl)-3,4,5,6-tetrahydropyridinium tetrafluoroborate To a stirred solution of 19.6 g. of 1,4,5-trimethyl-4-(3-methoxyphenyl)-1,4,5,6-tetrahydropyridine in 200 ml. of ethyl acetate containing 5 ml. of ethanol was added in one portion 10 g. of tetrafluoroboric acid-diethyl ether complex. The precipitate which formed was collected by filtration and recrystallized from 200 ml. of ethyl acetate and 5 ml. of ethanol to provide 9.43 g. of 1,4,5-trimethyl-4-(3-methoxyphenyl)-3,4,5,6-tetrahydropyridinium tetrafluoroborate. M.P. 126.5°–129° C.

Analysis calc. for $C_{15}H_{22}BF_4NO$: Theory: C, 56.62; H, 6.65; N, 4.40; Found: C, 56.90; H, 6.44; N, 4.43.

EXAMPLE 3

1,2,4,5-Tetramethyl-4-(3-methoxyphenyl)piperidine

A solution of 4.3 g. of 1,4,5-trimethyl-4-(3-methoxyphenyl)-3,4,5,6-tetrahydropyridinium tetrafluoroborate in 60 ml. of a 1.6 molar solution of methyl lithium in diethyl ether was stirred for two hours at 25° C. The reaction mixture then was diluted with 50 ml. of saturated aqueous ammonium chloride solution. The organic layer was separated, washed several times with water, dried and the solvent was removed by evaporation under reduced pressure to provide 3.2 g. of 1,2,4,5-tetramethyl-4-(3-methoxyphenyl)piperidine. The product thus formed was dissolved in 35 ml. of diisopropyl ether containing 1.5 g. of maleic acid in 75 ml. of ethyl acetate. The solid precipitate which formed was collected, dried and identified as 1,2,4,5-tetramethyl-4-(3-methoxyphenyl)piperidinium maleate. M.P. 119°–121.5° C.

Analysis calc. for $C_{20}H_{29}NO_5$: Theory: C, 66.09; H, 8.04; N, 3.85; Found: C, 65.88; H, 7.82; N, 3.72.

EXAMPLE 4

1,2,4,5-Tetramethyl-4-(3-hydroxyphenyl)piperidine

A solution of 900 mg. of 1,2,4,5-tetramethyl-4-(3-methoxyphenyl)piperidine in 10 ml. of glacial acetic acid containing 10 ml. of 48% aqueous hydrobromic acid was stirred at 25° C. for twenty-four hours. The reaction mixture then was diluted with water, made alkaline to pH 10 with sodium hydroxide, and the aqueous alkaline solution was extracted with diethyl ether. The ethereal extracts were combined, washed with fresh water and dried. Removal of the solvent by evaporation under reduced pressure afforded an oil. The oil so formed crystallized from ethyl acetate. Recrystallization of the product from 95 ml. of ethyl acetate afforded 640 mg. of 1,2,4,5-tetramethyl-4-(3-hydroxyphenyl)-piperidine. M.P. 207° C.(dec).

Analysis calc. for $C_{15}H_{23}NO$: Theory: C, 77.21; H, 9.94; N, 6.00; Found: C, 76.94; H, 9.76; N, 5.89.

EXAMPLE 5

Preparation of 1,5-dimethyl-4-n-propyl-4-(3-methoxyphenyl)-1,4,5,6-tetrahydropyridine Following the procedure set forth in Example 1, 43 g. of 1,5-dimethyl-4-n-propyl-4-(3-methoxyphenyl)-piperidine was reacted with 276 g. of mercuric acetate in 717 ml. of five percent aqueous acetic acid to provide, after purification by distillation, 30.2 g. of 1,5-dimethyl-4-n-propyl-4-(3-methoxyphenyl)-1,4,5,6-tetrahydropyridine. B.P. 126°–138° C. at 0.15 torr.

Analysis calc. for $C_{17}H_{25}NO$: Theory: C, 78.72; H, 9.71; N, 5.40; Found: C, 78.51; H, 9.55; N, 5.33.

EXAMPLE 6

1,5-Dimethyl-4-n-propyl-4-(3-methoxyphenyl)-3,4,5,6-tetrahydropyridinium tetrafluoroborate To a stirred solution of 14 g. of 1,5-dimethyl-4-n-propyl-4-(3-methoxyphenyl)-1,4,5,6-tetrahydropyridine in 50 ml. of diethyl ether was added in one portion 5 g. of tetrafluoroboric acid diethyl ether complex. The reaction mixture was stirred at 25° C. for two hours, and the precipitate which had formed was collected by filtration. The product thus obtained was recrystallized from 50 ml. of ethyl acetate and 50 ml. of ethanol to provide 14.31 g. of 1,5-dimethyl-4-n-propyl-4-(3-methoxyphenyl)-3,4,5,6-tetrahydropyridinium tetrafluoroborate. M.P. 159.5°–162° C.

Analysis Calc. for $C_{17}H_{26}BF_4NO$: Theory: C, 58.80; H, 7.54; N, 4.03; Found: C, 59.08; H, 7.37; N, 4.00.

EXAMPLE 7

1,2,5-Trimethyl-4-n-propyl-4-(3-methoxyphenyl)piperidine

A solution of 10 g. of 1,5-dimethyl-4-n-propyl-4-(3-methoxyphenyl)-3,4,5,6-tetrahydropyridinium tetrafluoroborate in 200 ml. of diethyl ether containing 100 ml. of 1.6 M methyl lithium in diethyl ether was stirred at ambient temperature for four hours. The reaction mixture then was washed with 100 ml. of saturated aqueous ammonium chloride, several times with water, and dried. Removal of the solvent by evaporation under reduced pressure afforded 9.4 g. of 1,2,5-trimethyl-4-n-propyl-4-(3-methoxyphenyl)piperidine.

A solution of 790 mg. of the product thus obtained was dissolved in 20 ml. of ethyl acetate and stirred while 340 mg. of maleic acid was added. The precipitate which formed was collected and dried and identified as 1,2,5-trimethyl-4-n-propyl-4-(3-methoxyphenyl)-piperidinium maleate. M.P. 114°–116° C.

Analysis calc. for $C_{22}H_{33}NO_5$: Theory: C, 67.49; H, 8.50; N, 3.58; Found: C, 67.29; H, 8.24; N, 3,88.

Following the procedure of Example 4, 1.1 g. of 1,2,5-trimethyl-4-n-propyl-4-(3-methoxyphenyl)piperidine was reacted with 25 ml. of forty-eight percent hydrobromic acid and 25 ml. of glacial acetic acid to provide, after isolation and purification by recrystallization from 100 ml. of ethyl acetate, 730 mg. of 1,2,5-trimethyl-4-n-propyl-4-(3-hydroxyphenyl)piperidine. M.P. 214°–215.5° C.

Analysis calc. for $C_{17}H_{26}NO$: Theory: C, 78.11; H, 10.41; N, 5.36; Found: C, 78.07; H, 10.13; N, 5.22.

I claim:

1. A compound having the formula

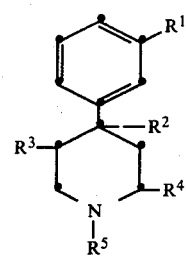

wherein:
$R^1$ is hydrogen, hydroxy or methoxy;
$R^2$, $R^3$ and $R^4$ independently are $C_1$–$C_5$ alkyl;
$R^5$ is $C_1$–$C_{10}$ alkyl, benzyl or $CH_2R^6$, in which $R^6$ is $C_2$–$C_7$ alkenyl or $C_3$–$C_6$ cycloalkyl; or a pharmaceutically acceptable acid addition salt thereof.

2. The compound of claim 1 wherein $R^5$ is $C_1$–$C_{10}$ alkyl.

3. The compound of claim 1 wherein $R^5$ is $CH_2R^6$.

4. The compound of claim 3 wherein $R^6$ is $C_2$–$C_7$ alkenyl.

5. The compound of claim 3 wherein $R^6$ is $C_3$–$C_6$ cycloalkyl.

6. The compound of claim 2 wherein $R^3$ and $R^4$ independently are methyl or ethyl.

7. The compound of claim 6 wherein $R^2$ is methyl, ethyl or n-propyl.

8. The compound of claim 2 wherein $R^1$ is hydrogen.

9. The compound of claim 2 wherein $R^1$ is methoxy.

10. The compound of claim 9 wherein $R^2$, $R^3$, $R^4$ and $R^5$ are methyl.

11. The compound of claim 9 wherein $R^2$ is n-propyl, $R^3$, $R^4$ and $R^5$ are methyl.

12. The compound of claim 2 wherein $R^1$ is hydroxy.

13. The compound of claim 12 wherein $R^2$, $R^3$, $R^4$ and $R^5$ are methyl.

14. The compound of claim 12 wherein $R^2$ is n-propyl, $R^3$, $R^4$ and $R^5$ are methyl.

15. A pharmaceutical formulation useful in the treatment of pain in animals comprising an analgesically effective amount of a compound of claim 1 in combination with a suitable carrier therefor.

16. The formulation of claim 15 wherein the active ingredient has the formula

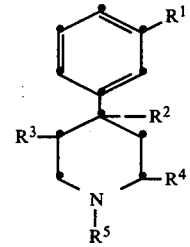

wherein
$R^1$ is hydroxy or methoxy;
$R^2$ is $C_1$–$C_3$ alkyl;
$R^3$ and $R^4$ are methyl; and
$R^5$ is $C_1$–$C_5$ alkyl 17. A method of inducing analgesia in animals comprising administering an analgesically effective dose of a compound of claim 1.

18. The method of claim 17 wherein in the compound administered, $R^1$ is hydroxy or methoxy, $R^2$ is $C_1$–$C_3$ alkyl, $R^3$ and $R^4$ both are methyl and $R^5$ is $C_1$–$C_5$ alkyl.

19. The method of claim 18 wherein in the compound administered, $R^1$ is hydroxy, $R^2$ and $R^5$ are methyl.

20. The method of claim 18 wherein in the compound administered, $R^1$ is methoxy, $R^2$ and $R^5$ are methyl.

21. The method of claim 18 wherein in the compound administered, $R^1$ is methoxy, $R^2$ is n-propyl, and $R^5$ is methyl.

22. The method of claim 18 wherein in the compound administered, $R^1$ is hydroxy, $R^2$ is n-propyl and $R^5$ is methyl.

* * * * *

UNITED STATES PATENT AND TRADEMARK OFFICE
CERTIFICATE OF CORRECTION

PATENT NO. : 4,284,635
DATED : August 18, 1981
INVENTOR(S) : Dennis M. Zimmerman It is certified that error appears in the above-identified patent and that said Letters Patent are hereby corrected as shown below:

Column 4, lines 15-25, the formula should read as follows:

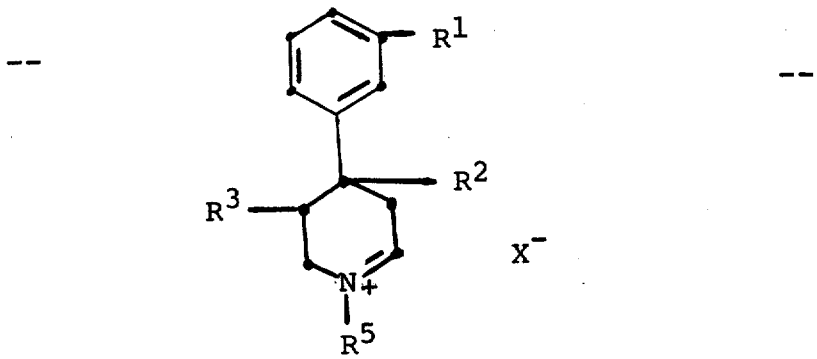

Signed and Sealed this

Second Day of February 1982

[SEAL]

Attest:

GERALD J. MOSSINGHOFF

Attesting Officer      Commissioner of Patents and Trademarks